(12) United States Patent
Tvedten

(10) Patent No.: US 6,663,860 B1
(45) Date of Patent: Dec. 16, 2003

(54) BIOLOGICAL PESTICIDE

(75) Inventor: Stephen L. Tvedten, 2530 Hayes St., Marne, MI (US) 49435-9751

(73) Assignee: Stephen L. Tvedten, Marne, MI (US)

( * ) Notice: Subject to any disclaimer, the term of this patent is extended or adjusted under 35 U.S.C. 154(b) by 0 days.

(21) Appl. No.: 09/341,174

(22) PCT Filed: Jan. 8, 1998

(86) PCT No.: PCT/US98/01137

§ 371 (c)(1),
(2), (4) Date: Aug. 20, 1999

(87) PCT Pub. No.: WO98/30236

PCT Pub. Date: Jul. 16, 1998

(51) Int. Cl.$^7$ .......................... A61K 38/48; A61K 38/43
(52) U.S. Cl. .............. 424/94.63; 424/94.64; 424/94.65; 424/94.66; 424/94.2; 424/94.1; 424/84; 435/212
(58) Field of Search .................. 424/94.63, 94.64, 424/94.65, 94.66, 94.2, 94.1, 84; 435/212

(56) References Cited

U.S. PATENT DOCUMENTS

| | | | |
|---|---|---|---|
| 3,404,068 A | | 10/1968 | Battistoni |
| 3,561,944 A | | 2/1971 | Battistoni et al. |
| 3,635,797 A | | 1/1972 | Battistoni et al. |
| 3,873,700 A | * | 3/1975 | Misato et al. ............... 424/199 |
| 4,826,682 A | * | 5/1989 | Sakharova ................... 424/623 |
| 5,158,595 A | | 10/1992 | Stillman |
| 5,160,525 A | | 11/1992 | Stillman et al. |
| 5,820,758 A | | 10/1998 | Dale et al. |
| 5,849,566 A | | 12/1998 | Dale et al. |
| 5,879,928 A | | 3/1999 | Dale et al. |
| 5,885,950 A | | 3/1999 | Dale et al. |
| 5,935,572 A | * | 8/1999 | Hayward et al. .......... 424/94.2 |

FOREIGN PATENT DOCUMENTS

| | | | |
|---|---|---|---|
| EP | 0 184 288 | * | 6/1986 |
| WO | 9119417 | | 12/1991 |
| ZA | 698059 | | 11/1969 |

OTHER PUBLICATIONS

Irwin H. Segel, Biochemical Calculations, John Wiley & Sons, New York, pp 273–277, 1976.*

*The Condensed Chemical Dictionary*, 8$^{th}$ Edition, Hawley Editor, Van Norstrand Reinhold Company, New York, p. 133, 1974.*

Biological Abstracts, vol. 70, No. 4, 1980, (Columbus, Ohio, USA), abstract No. 25895, Kucera et al., 'Partial purification and properties of proteases of bitoxibacillin.' Prikl. Biokhim. Mikrobiol. 15 (5), 1979, 707–711, see entire abstract.

Chemical Abstracts, vol. 124, No. 5, Jan. 29, 1996, (Columbus, Ohio, USA), p. 449, col. 2, abstract No. 48341t, XIE, Y., 'Insecticide containing protease and sulfur.' CN 1,105,515, Jul. 26, 1995, see entire abstract.

Chemical Abstracts, vol. 119, No. 9, Aug. 30, 1993, (Columbus, Ohio, USA), p. 412, col. 1, abstract No. 88960x, Matsushita, T., 'Insecticides containing boric acid solutions incorporated into Saccharomyces.' JP 05–124,908, May 21, 1993, see abstract.

Chemical Abstracts, vol. 109, No. 21, Nov. 21, 1988, (Columbus, Ohio, USA), p. 261, col. 2, abstract No. 185488a, Zoelde, R., 'Ingestion insecticide containing carbon dioxide–releasing agents.' DE 3,712,487, Aug. 18, 1988, see entire abstract.

Fumio Matsumara, Toxicology of Insecticides, Chapter 6, Entry of Insecticides into Animal Systems, pp. 253–274 (1976).

* cited by examiner

Primary Examiner—Francisco Prats
(74) Attorney, Agent, or Firm—Price, Heneveld, Cooper, DeWitt & Litton

(57) ABSTRACT

Methods for exterminating pests using compositions comprising at least one protease enzyme. A detergent component may also be utilized in such compositions.

77 Claims, No Drawings

BIOLOGICAL PESTICIDE

BACKGROUND OF THE INVENTION

Pesticides are commonly used in a multitude of settings, from homes, schools, and offices to manufacturing plants, cargo containers, and agricultural contexts. Most pesticides are generally insect or arachnid nervous system toxicants, inhibiting or overpotentiating synapse-synapse and/or neuro-muscular junction transmission, many acting specifically as acetylcholinesterase inhibitors.

Representative examples of pesticides include: 1) chlorinated phenyl and cyclodiene compounds such as DDT, chlordane, heptachlor, and aldrin and dieldrin; 2) the carbamate esters carbaryl, carbofuran, aldicarb, and baygon; 3) organic thiophosphate esters such as diazinon, malathion, parathion, and dicapthon; and 4) the synthetic pyrethroids allethrin, permethrin, resmethrin, and fenvalerate.

These and other pesticides present risks to human health. Although the rate of post-application degradation may vary widely, almost all pesticides present some direct risk to human health through residual toxicity, i.e. direct human contact with pesticide residues remaining after treatment, whether through inhalation of volatile toxic vapors, skin contact and transdermal absorption, or ingestion. In addition, many pesticides present indirect risks to human health in the form of environmental pollution, most notably pollution with persistent, halide-substituted organics which accumulate in the fat stores of food fish and other animals. These problems have led to complete bans on the use of some pesticides—e.g., DDT, chlordane, heptachlor, aldrin, and dieldrin—while the continued use of the remaining pesticides has produced a new problem: the increasing development of widespread resistance to pesticides.

This resistance yields two results: 1) quick post-treatment reoccupation, by the same or a similar insect or arachnid, of the pesticidally-cleared area, and 2) the need and cost of continually engineering new pesticides (e.g., synthetic pyrethroids were developed because of resistance to the less toxic first generation pyrethrins). New pesticide production takes time and the new pesticides that result are almost universally more expensive than those they replace. In this context, traditional pesticides are applied on a regular, and typically increasing, basis. For example, many schools have come to be sprayed monthly or even biweekly, and with increasing quantities of pesticides to combat endemic roach re-infestations, often to no avail. This intensifies the problem of residual toxicity to people, especially to children who, as a result, may suffer headaches, grogginess, nausea, dizziness, irritability, frenetic behavior, and an impaired readiness to learn.

Because of these effects, it has been recognized that totally new approaches must be discovered and implemented in order to effectively control invertebrate pests without destroying human health and the environment. One such approach is "integrated pest management" ("IPM").

Integrated pest management utilizes a variety of ecological strategies by taking advantage of pest behaviors and natural enemies, such as parasites, predators, and/or diseases. Examples of such strategies include the use of commercially available supplies of ladybugs to treat aphid infestations, the release of sterile males into populations of pests to decrease their genetic potential, the trapping or bait-poisoning of pests responding to a pheromone attractant, the application of juvenizing hormones to pests, and the release of spores of pest-pathogenic bacteria such as *Bacillus thuringiensis*.

Usually a variety of these techniques must be used together since few result in broad-spectrum pest control. However, their use alone takes a significant investment of time, labor, and attention in order to attain a threshold level of pest control: pest populations must be monitored and recorded, occupants may be required to improve their housekeeping habits, and structural problems such as cracks and gaps must be identified and repaired. In addition, it is often necessary to quickly combat acute infestations, requiring treatment with traditional pesticides in the short term, in order to readily establish the long-term controls of IPM. Moreover, many of the ecological strategies have limited applicability in indoor environments such as offices and classrooms. Therefore, there is a need for a quick-acting, effective, residually non-toxic method for combatting insect, arachnid, and other pests which may be used as a replacement for traditional pesticide treatments and as a supplement to the arsenal of currently available IPM techniques.

SUMMARY OF THE INVENTION

Consequently, it is an object of the present invention to provide a method for combatting invertebrate (i.e. insect and arachnid) and microbe (i.e. bacterial, algal, fungal, and/or viral) pests which is quick-acting, effective, and residually non-toxic and which may be used as a replacement for traditional pesticide treatments and as a supplement to the arsenal of currently available integrated pest management techniques.

It has been surprisingly found that the application of a composition comprising at least one protease enzyme is a method for exterminating pests which achieves these objectives. The enzyme component of the invention may comprise a single protease or a protease-containing mixture of enzymes, whether natural, preformed, or synthetic. In an alternate embodiment, the composition may also comprise a detergent component. This detergent component comprises one or more surfactant(s), detergent builder(s), or mixtures thereof.

DETAILED DESCRIPTION OF THE PREFERRED EMBODIMENTS

A preferred embodiment of the method of the present invention employs a composition comprising an enzyme component. The enzyme component comprises at least one protease enzyme which may be a natural, preformed, or synthetic protease, alone or in combination with other enzymes. The protease(s) used in the composition of a preferred embodiment of the present invention may be any of the peptidases, serine proteases, zinc proteases, thiol proteases, and/or acid proteases. The protease(s) may be digestive protease(s) from an animal, plant, bacterium, or fungus. Additional enzyme(s) may be any of hydrolases, oxidoreductases, transferases, lyases, ligases, and/or isomerases. The additional enzyme(s) may comprise digestive enzyme(s) from an animal, plant, bacterium, or fungus. Preferably, the enzyme component comprises at least one protease and at least one other hydrolase, more preferably a mixture of at least one protease and at least one cellulase, lipase, glycosidase, amylase, chitinase, other protease, or mixture thereof.

Protease enzymes may be obtained from various commercial sources. A preferred protease source is the mixture of proteases—IUB 3.4.21.14 and IUB 3.4.24.4—sold as Burcotase AL-25 and available from Burlington Chemical Co. of Burlington, N. C. Preferably about 20% by weight or less of the composition will comprise enzymes, more preferably about 0.3–10%, even more preferably about 1–5%, and still more preferably about 5%.

The enzyme(s) used in the composition of a preferred embodiment of the present method are dissolved or suspended in water. In an alternate embodiment, they may be dissolved or suspended in a solution comprising a detergent component.

The detergent component may comprise one or more surfactants—e.g., soap(s), —detergent builders, or mixtures thereof. The surfactant may be one or more of the cationic, anionic, nonionic, zwitterionic, amphoteric, amphiphilic, or ampholytic surfactants, the soaps, or the mixtures thereof. Preferably, the detergent component will comprise at least one surfactant, more preferably at least one surfactant and at least one detergent builder, and even more preferably at least one detergent builder and a peppermint soap. Alternately, the detergent component will preferably comprise at least one each of anionic and nonionic surfactants, and a peppermint soap, and more preferably, at least one detergent builder, at least one each of anionic and nonionic surfactants, and a peppermint soap.

Preferred anionic surfactants include alkali metal-, alkaline earth metal-, ammonium-, and alkylammonium- carboxylate, -sarcosinate, -sulfonate, and -sulfate salts of saturated or unsaturated alkyl, aryl, or alkylaryl compounds. More preferred anionic surfactants include the salts of saturated and unsaturated alkyl alcohols, fats, fatty acids, and oils, including tallow or coconut, palm, castor, olive, or citrus oils. Even more preferred anionic surfactants include the alkali metal, alkaline earth metal, ammonium, and alkylammonium salts of $C_8$–$C_{20}$ alcohol sulfates and of $C_8$–$C_{20}$ fatty acids.

Preferred nonionic surfactants include alkoxylated and polyalkoxylated compounds. More preferred nonionic surfactants include ethoxylated- and polyethoxylated- alkylphenols, -alcohols, -polyols, -fatty acids, -fatty acid amides, and -carboxylic acids. Even more preferred nonionic surfactants include the alkylaryl polyethylene glycols, e.g., alkylphenvl ethers of polyethylene glycol.

Preferred soaps may be one or more of the natural soaps, neat soaps, insecticidal or antibacterial soaps; the oil soaps or castile soaps; the household or commercial cleaners or degreasers; the oil-spiked, extract-spiked, or saponified botanical oil-based soaps such as soaps comprising, e.g., an oil, saponified oil, or extract of citronella (or citronellol or rhodinol), pine (or terpineol), cedarwood, sandalwood. wormwood, lemon grass. citrus (e.g., lemon), lavender, eucalyptus, sassafras, neem tree, balsam, niaouli, cajeput, clove, cubeb, thyme, garlic, wintergreen, peppermint or another mint, American wormseed, Levant wormseed, Juniperus spp., or Chrysanthemum spp., or comprising, e.g., an additive such as menthol, menthane, sobrerol, camphor, or anethole, or comprising a mixture thereof; or the mixtures thereof. Preferably, the soap-type surfactant will comprise a peppermint soap, i.e. a soap preparation comprising a peppermint oil or peppermint extract additive or a saponified peppermint oil.

Preferred detergent builders include the alkali metal- borates, -tripolyphosphates, -pyrophosphates, -phosphates, -sesquicarbonates, -carbonates, -silicates, -aluminosilicates, -nitrilotriacetates, -citrates, -EDTAtes, and mixtures thereof. A most preferred builder is sodium borate.

In a preferred embodiment, the detergent component will make up about 85% or less by dry weight of the composition. Preferably, about 85% or less by dry weight of surfactants are used in the composition, more preferably about 75% or less. Where a mixture of surfactant(s) is utilized, about half or more of the surfactants may preferably be anionic (at least about 50±25% by weight) and about half or less may preferably be nonionic (as much as about 50±25% by weight). The composition may comprise, as part of the detergent component, preferably about 25% or less by dry weight of soap(s), more preferably about 5–15%, and still more preferably about 5–10%. Where the detergent component comprises detergent builder(s), either alone or together with surfactant(s), e.g., soap(s), preferably about 50% or less by dry weight of the composition comprises builder, more preferably about 2–10%, and still more preferably about 5%.

Commercially available enzyme and surfactant mixtures or enzyme-containing fermentation products can be employed in a preferred embodiment. A preferred mixture is Bacto-Zyme produced by International Enzymes, Inc. of Las Vegas, Nev.; other preferred enzyme mixtures are sold as the "150," "150N," "300," and "300N" products available from Great Lakes Biosystems, Inc. of Kenosha, Wisconsin. Bacto-Zyme comprises proteases, lipases. cellulases, and amylases, among other enzymes. Such mixtures and products may be prepared according to the methods taught in U.S. Pat. No. 3,561,944, U.S. Pat. No. 3,635,797, and ZA 6,908,059 (South Africa) to Battistoni et al. These are formed by means of enzymatic fermentation of a mixture comprising a simple sugar source, a starch source, and a magnesium salt, preferably magnesium sulfate. The simple sugar source may comprise a molasses and/or a sugar, e.g., raw or refined cane or beet sugar. The simple sugar source is optional; when used, it may also be substituted or supplemented with kelp. The starch source may be one or more fermentable carbohydrate sources, such as barley, wheat, oat, millet, rice, corn, tapioca, potato, sago, canna, dasheen, legume (i.e. bean or pea), or other cereal grain or plant carbohydrate storage organ malt or mash, or a mixture thereof. Preferably, barley malt or oat malt or a mixture thereof is utilized. Fermentation may be carried out using a baker's or brewer's yeast, i.e. one or more strains of *Saccharomyces cerevisiae, Saccharomyces carlsbergensis*, or mixtures thereof. Upon completion of fermentation, at least one surfactant and/or other supplement is added to the fermentation product to form a mixture. Where such a fermentation product or fermentation-surfactant mixture is used, the composition will comprise preferably about 10–65% by dry weight (i.e. including the water content of molasses, but excluding the weight of added water) of it, more preferably about 20–50%, and still more preferably about 25–50%. The commercially available enzyme and surfactant mixtures—or the commercially available enzyme-containing fermentation products themselves—may be supplemented with any of the surfactants (e.g., soaps) and/or enzymes as described above. Likewise, enzyme-free fermentation products resulting from fermentation of any of the above-described starch sources, followed by purification to remove such enzymes, may be supplemented with any of the surfactants (e.g., soaps) described above and any protease or a protease-other enzyme mixture as described above.

Irrespective of which source(s) of enzymes and/or surfactants is utilized, various nitrogen source(s), acid source (s), buffer(s), oil(s), extract(s), and/or other additive(s) may also be included in the composition. Preferred nitrogen sources include, but are not limited to, urea, ammonium sulfate, and mixtures thereof. When used, the nitrogen source may be present in amount up to about 45% by dry weight of the composition. Where the composition comprises urea, it is preferably about 40% or less by dry weight of the composition, more preferably about 1–30%, even more preferably about 5–30%, still more preferably about 10–30%. If ammonium sulfate is utilized, preferably about 30% or less by dry weight is present, more preferably about 0.5–30%, still more preferably 0.5–20%.

Preferred acid sources include, but are not limited to, one or more of acetic acid, ascorbic acid, citric acid, lactic acid, succinic acid, fumaric acid, tartaric acid, and phosphoric acid, ammonium and/or metal ion salts thereof, or mixtures thereof; more preferably, the acid source comprises citric acid, lactic acid, ascorbic acid, or a mixture thereof. Up to about 15% by weight of the composition may comprise an acid source. Where citric acid is used, it is preferably about 0.5–5% by dry weight of the composition, more preferably about 1–2%; where lactic acid is employed, it is preferably about 2–10% by dry weight, and more preferably about 4–8% by dry weight.

Preferred oils and extracts include, but are not limited to: botanical oils and essential botanical extracts such as those of citronella (and citronellol and rhodinol), pine (and terpineol), and cedarwood, sandalwood, wormwood, lemon grass, citrus—e.g., lemon,—lavender, eucalyptus, sassafras, neem tree, balsam, niaouli, cajeput, clove, cubeb, thyme, garlic, wintergreen, peppermint and other mints, American wormseed, Levant wormseed, Juniperus spp., and Chrysanthemum spp.; menthol, menthane, sobrerol, camphor, and anethole; and mixtures thereof. The composition may comprise preferably about 5% by weight of the composition or less of oil(s) and/or extract(s), more preferably about 0.1–5% by dry weight of the composition.

Water is also present in the composition. The amount of water present in the composition may preferably range from about 60% to about 99.5% by weight of the composition.

Other optional additives that may be included in the composition include, but are not limited to: alcohols, hydrogen peroxide, glycerin, and borax; sugar sources, e.g., honey, sucrose, corn syrup, molasses, etc.; pest pheromones, pheromone analogs, and pheromone-type attractants, e.g., phoromone, 4-methyl-3-heptanone, and pest-attractive organoborane derivatives; pest hormones, growth regulators, and their analogs, e.g., methyl 12,14-dihomojuvenate, methyl 12-homojuvenate, methoprene, hydropene, fenoxycarb, lufenuron, diflubenzuron, hexaflumuron, and cyromazine; botanical pesticides, e.g., rotenone, ryania (and ryanodine), sabadilla, hellebore, limonene, linalool, and nicotene: aluminum-containing compounds of which aqueous solutions or slurries may be formed; and mixtures thereof.

Preferred aluminum compounds include, for example: aluminum-halogen compounds. such as $AlCl_3$, $AlCl_3(H_2O)_6$, $Al_2(OH)_5Cl$, $AlCl_3O_9$, and $Al[CO(NH_2)_6]SO_4]_3$, aluminum-silicon compounds, such as $Al_2(SiF_6)_3$ and $MgAl_2(SiO_4)_2$; aluminum hydroxides, e.g., $Al(OH)_3$, and aluminum-containing organic compounds including carboxylates of the formula $Al(OH)_{3-n}(R)_n$ wherein n is 1, 2, or 3—e.g., aluminum diformate, diacetate, or subacetate—and $Al_2[C_{10}H_5(OH)(SO_3)_2]_3$; aluminum-carbonate compounds, such as $Al_2(CO_3)_3$; aluminum-phosphorous compounds, such as $AlPO_4$; aluminum-sulfates, e.g., $Al_2(SO_4)_3$, and alums, e.g., $NaAl(SO_4)_2$; aluminates, such as $NaAlO_2$; aluminum-nitrate compounds, such as $Al(NO_3)_3$, $Al(OH)_2(NO_3)$, and $Al(OH)(NO_3)_2$; and mixtures thereof. Where an aluminum compound is added to the composition, it may preferably be present at a concentration sufficient to provide about 1% w/v or less of aluminum, more preferably about 0.5% w/v or less of aluminum. Preferably, the majority of the aluminum will be present in the form of dissolved aluminum ion, $Al^{3+}$. Where substantially all of the aluminum is present as dissolved $Al^{3+}$, preferably about 0.4% w/v of aluminum may be used.

The pH of the composition may be controlled using the acids described above and may also be controlled using buffer systems such as are known in the art. It is usually desirable to maintain a pH of about 2 to about 12, and often preferable to maintain a pH of about 4 to about 10. Rarely, a pH of about 1 may be employed. The pH of the composition may be tailored to the optimal point, i.e. pH or pH range, for enzymatic activity. For example, the pH may be acidified and/or buffered either to the approximate optimal point for protease activity or to some optimal intermediate point when a mixture of enzymes is utilized. A pH of about pH5 is frequently preferred as an approximate optimal point when acid proteases are used. The optimal point for the protease mixture of Burcotase AL-25 is the range of about pH7 to about pH10.

In a preferred embodiment of the method of the present invention, the enzymatic composition may be applied using any techniques known in the art. For example, it may be applied by spraying, pressurized spraying, streaming, injecting, pouring, soaking, flooding, splashing, splattering, sprinkling, dripping, drizzling, shampooing, foaming, washing, mopping, wiping, spreading, scattering, absorbing, adsorbing, misting, vaporizing, and/or fogging said composition, bathing and/or soaking in said composition, and/or retaining a pool of said composition. Such preferred embodiments may further employ one or more baiting technique(s) in which a pest attractant (e.g., dry ice as a carbon dioxide attractant) is used in or in conjunction with said composition. In any application or technique used, the enzymatic composition must contact the body—e.g., head, thorax, and/or abdomen—of the pest for the method to work. The concentration of the composition and/or the volume of composition to be applied may depend on the species of pest infesting the site to be treated.

The optimal mode(s) of application will vary with the type of pest and specific environmental conditions present at an infestation site. In some cases it is desirable to use a direct contact mode of application and, e.g., a spraying technique will be employed. Where pests are located in less accessible places such as in structural cracks in or behind structural gaps in a building, pavement, fixture, article of furniture, or in tree bark, either an injection or a pressurized spraying technique is typically preferred. A preferred direct mode of application for structure damaging pests comprises injecting the composition, e.g., into "galleries" within the structure where the pest colonies are located.

Where the infestation comprises an ectoparasite or a dermal, fur, hair, down, or feather pest of a mammal, bird, reptile, or plant, e.g., lice, fleas, mites, chiggers, or fungi, a preferred technique involves shampooing and/or washing with said composition. Where the infestation comprises a burrowing parasite or intradermal pest, e.g., scabies, mites, or springtails, a preferred technique involves bathing and soaking in said composition.

Other preferred modes include indirect contact modes wherein the composition may be applied to a pest-accessible surface so that an insect or arachnid pest may "voluntarily" come into contact with the composition. With some pests, e.g., scorpions, a water-trap technique may be preferred in which a container retaining a pool of the composition is set out and when the pest approaches the pool, it contacts the enzymatic composition or even falls into the pool, and drowns and/or is dissolved. In another preferred indirect mode of application for structure-damaging pests such as drywood termites, the composition is suffused or soaked into or onto a structural object such as a piece of wood which is within, or is placed within, the reach of the pests. In this technique, the structural object must be made of a pest-chewable substance, i.e. a substance which is ingestible or digestible by the pest or is pierceable by or manipulable by the mandible(s), palp(s), pincer(s), or proboscis of the pest. In this way, the pest can come into contact with the enzymatic composition.

The indirect modes of application may also comprise baiting said composition by adding an insect or arachnid pest attractant to the composition or otherwise employing a pest attractant in conjunction with the composition. For example, the composition may comprise bait such as: a sweet attractant, e.g., a fermentation product or sugar source as described above; a pest pheromone-type attractant such as a pest pheromone, pheromone analog, or pheromone-type attractant as described above; a carbon dioxide attractant, e.g., chunks of dry ice or a stream of bottled carbon dioxide gas; and or a light attractant comprising a waterproof light, whether continuous or blinking, white or colored, may be added to the composition. Where the bait is used in conjunction with the composition, a sweet or pheromone attractant, a carbon dioxide attractant—such as dry ice, a candle flame or other combustion flame, or a stream of bottled carbon dioxide gas—and/or a light attractant—i.e. a continuous or a blinking light, whether white or colored (e.g., green or "black" light)—is placed, e.g., adjacent to or above the composition. A preferred baiting technique involves placing one or more pest pheromone packet(s), above the level of the composition, upon the inside walls of a container partially filled with the composition. Another preferred baiting technique involves placing a continuous white or black light or a blinking green light above an open container of the composition. A further preferred baiting technique comprises placing a candle or other combustion flame above a pool of the composition, e.g., by affixing a vertically standing candle to the bottom of the composition-containing pool, or where a ring-shaped container is employed, placing the burning candle or other combustion flame within the ring. The site of the attractant may, additionally or alternatively, be periodically sprayed, misted, or fogged with the composition.

The method of the present invention has been found effective against invertebrate pests at all stages of development, from egg to larva to adult. In many cases it is also effective at dissolving the nest of the pest: for example, paper wasp nests and the immature pests they contain can be disintegrated on contact. A non-exhaustive list of pests which have been successfully eradicated by the method of the present invention includes black ants, fire ants, carpenter ants, Pharaoh ants. termites, roaches (all varieties tested), bark lice, book lice, hair lice, crab lice, body lice, louse nits, fleas, scabies, psocids, scale insects, bees, wasps, hornets, yellowjackets, bedbugs, earwigs, silverfish, springtails, sowbugs, pillbugs, millipedes, centipedes, gnats, fungus gnats. midges, dust mites, chiggers, bird mites, skin mites, spider mites, spiders, scorpions. mosquitoes, fruit flies, horse flies, deer flies, house flies, maggots, sewer flies, black flies, moths, fabric moths, gypsy moths, tent moths, beetles, carpet beetles, drug store beetles, crickets, grasshoppers, aphids, grubs, cutworms. slugs, pet and cattle pests, fabric and pantry pests, occasional invaders, soil pests, and lawn, garden, orchard, crop, and forestry pests including ectoparasites of bark, leaves, roots, shoots, seeds, fruits, and so forth. The method of the present invention has also been found effective at decreasing or eliminating the incidence of allergic reaction to dust. Although not wishing to be bound to any particular theory, it is believed that this decreased incidence of allergic reaction may be due to the enzyme's or enzymes' degradation of allergenic dust mite proteins.

The method of the present invention has also been found effective against microbe pests including bacteria, algae, and fungi. For example, algae and organic debris present as undesireable material filling ponds have been eliminated by applying the enzyme-containing composition of the present invention to the pond water and mixing it therewith. Although not wishing to be bound to any particular theory, it is believed that this effect is a result of the enzymes or enzymes' destruction of, e.g., the algal mats by degrading the cell walls of the algae and the peptidomucous making up these mats.

In addition, the method of the present invention has been found effective at eliminating fungal infestations. For example, application of the enzyme-containing composition according to the method of the present invention has eliminated: powdery mildew, copper spot, sooty mold, Pythium blight, fruit rot molds, Fusanum, Septoria leaf spot, Puccinia spp. rusts, and various smuts from growing plants; and ringworm fungus, athlete's foot fungus, and jungle rot fungus infestations from mammals. Such treatment has also been found effective to control scalpal, fungal seborrheic dermatitis on mammals. Application of the enzyme-containing composition of the present invention has also been found to eliminate the incidence of (airborne) fungal-based allergic reactions in the indoor environment.

Moreover, in testing the methods of the present invention, it has been found that, by altering the concentration of the enzyme-containing pesticidal composition, certain insect pest species may be killed while others will survive treatment. For example, at a 1:500 water dilution, the enzyme-containing, pesticidal composition has been found to kill soft-shelled pests including aphids, leaf miners, and mites, while having little or no effect on either beetles, such as the beneficial lady bug beetles, nor Aschersonia species of beneficial fungi. However, at much higher concentrations all insects, including beetles, were destroyed.

EXAMPLE 1

A solution of Bacto-Zyme cleaner (containing enzyme(s) and surfactant(s)) was prepared by combining 1 part by volume of Bacto-Zyme with 8 parts by volume water and a sprayer was filled with this solution. A grammar school building in which a 4 inch wide column of army ants extended throughout the entire length of the main hallway was sprayed and the column was sprayed back to the ants' point of entry, which was also copiously sprayed. The ants were dissolved on contact and their scent trail was apparently destroyed, as no further ants appeared following treatment.

EXAMPLE 2

A solution as prepared in Example 1 was sprayed throughout a grammar school building in which roaches, at night, were seen to be covering over 75% of available wall and floor surfaces, in spite of heavy, regular applications of traditional pesticides. The roaches were quickly dissolved. Copious spraying was then continued in and around the sinks, drains, and structural cracks and gaps of the building. No live roaches were noted in the building for approximately 3 months thereafter.

EXAMPLE 3

A concentrated solution was prepared as follows. 5% by weight of Burcotase AL-25 was dissolved in a castile soap solution comprising 5% by weight of sodium borate and 5% peppermint oil. This concentrate was diluted 1 part in 4 with water to form a working solution. This solution was sprayed in an elementary school building which was heavily and regularly treated—to no avail—with traditional pesticides to combat a round-the-clock Oriental roach infestation. The drains, gaps, cracks, and the areas beneath the sinks were also copiously sprayed according to the method of the present invention, and the carpeted areas were shampooed therewith. No more roaches appeared for over 4 months following treatment.

EXAMPLE 4

A 10 gallon carboy was filled with a solution as prepared in Example 1. An anthill 5 feet in diameter, housing a large black ant colony in a farm field was soaked with the enzymatic solution. The colony was completely destroyed and the anthill collapsed on itself.

EXAMPLE 5

A pharmacy which had a persistent drug store beetle infestation under the surface of the countertop was sprayed with the solution as prepared in Example 1 and the solution was injected into the space beneath the countertop. In spite of the resilience of this species of beetle (they are known to eat strychnine and pyrethrin-type pesticides), the method of the present invention permanently eliminated this entrenched infestation.

EXAMPLE 6

A house with a Pharaoh ant infestation was treated according to the method of the present invention. Prior, traditional pesticide treatment of the single colony living within the confines of the house had, predictably, triggered the natural response of this species to divide the colony. As a result, there were now at least three colonies living within the confines of the house. Treatment of the infestation with the solution as prepared in Example 1, according to the method of the present invention, eliminated all three colonies and no colony subdivisions were formed.

EXAMPLE 7

A school wherein over 50% of students had chronic head lice reinfestations was treated according to the method of the present invention. In spite of the teachers' and parents having tried three commercially available products as well as repeatedly laundering all clothes and fabrics, the reinfestation problem remained. The school was sprayed and shampooed with the solution as prepared in Example 1. The source of the infestation was eliminated and the reinfestation problem was resolved.

Although not wishing to be bound to any particular theory, it is believed that the method of the present invention works as follows. Upon contact with an invertebrate pest, the protease(s) may directly attack the protein zipper which holds the halves of the insect or arachnid exoskeleton together, normally until molting begins, or may attack the substance of the proteinaceous body of other invertebrate, e.g., mollusk, pests. The use of a detergent component in the enzymatic composition may enhance this action by allowing the composition to penetrate any waxy cuticle or proteinaceous coating covering the body of the pest. This appears to permit the enzyme(s) of the composition to penetrate to the exoskeleton or body itself. Where cellulase(s), amylase(s), glycosidase(s), and/or chitinase(s) are used along with the protease(s), they may directly attack the matrix of the insect, arachnid, or crustacean exoskeleton, which is often composed of chitin, a cellulose derivative. The differing types and/or thicknesses of exoskeleton in different pest species may account for the need to apply a greater volume or concentration of the composition in some cases than in others. Where the pest ingests the composition, the enzymes therein may also cause internal degradation in the pest. It is believed that enzymatic attack to the body of the pest, whether by such, or other, routes, may likely be responsible for the effective killing action afforded by the present method. Because, in the above-described preferred embodiments, a detergent component is employed in the composition, the method of the present invention is typically self-cleaning, thus helping to provide residual non-toxicity.

The advantages of the methods and compositions described herein are seen in that the widespread use of large quantities of costly synthetic organic pesticides may be significantly reduced or replaced by the methods of the present invention. For example, the practice of spraying highly toxic methyl bromide upon fruit and nut groves may be effectively replaced with the use of inexpensive, low- and non-toxic enzyme-containing compositions according to the methods of the present invention.

Variations of the methods and compositions described herein as a preferred embodiment may be apparent to those skilled in the art once they have studied the above description. For example, it may be apparent that the composition utilized in the present method may be solutions or suspensions of one or more of the commercially available protease enzyme-containing products, such as enzyme-containing meat tenderizers, digestive aids, fabric detergents, stain removers, dishwashing products, household cleaners, water treatments, sewage treatments, and so forth. Variations such as these are considered to be within the scope of the invention, which is intended to be limited only to the scope of the claims and the reasonably equivalent materials and methods to those defined therein. The foregoing examples illustrate a preferred embodiment of the invention. Various changes can be made without departing from the invention as defined in the appended claims, which are to be interpreted in accordance with the principles of patent law including the Doctrine of Equivalents.

What is claimed is:

1. A method for exterminating pests comprising the steps of providing a composition comprising an enzyme component, said enzyme component comprising at least one protease, and a detergent component, said detergent component comprising a surfactant and a detergent builder; and applying said composition to a pest.

2. The method according to claim 1 wherein said step of applying said composition to said pest comprises a first substep and a second substep, the first substep selected from the group consisting of applying said composition to at least one pest-accessible surface to form a layer on said surface, suffusing at least one pest-chewable substance with said composition, and at least partially filling a pest-accessible container to form a pest-accessible pool of said composition, and the second substep comprising allowing said pest to contact said layer with at least one part of its body.

3. The method according to claim 1 wherein said step of applying said composition comprises using a technique selected from the group consisting of spraying, pressurized spraying, streaming, injecting, pouring, soaking, flooding, splashing, splattering, sprinkling, dripping, drizzling, shampooing, foaming, washing, bathing in, soaking in, mopping, wiping, spreading, scattering, absorbing, adsorbing, misting, vaporizing, and fogging said composition.

4. The method according to claim 2 wherein said method further comprises a baiting substep comprising a baiting technique selected from the group consisting of adding at least one pest attractant to said composition before said first substep and placing at least one pest attractant adjacent to or above said composition before said second substep.

5. The method according to claim 4 wherein said pest attractant is selected from the group consisting of sweet attractants, pheromone attractants, carbon dioxide attractants, light attractants, and mixtures thereof.

6. The method according to claim 5, wherein said pest attractant is selected from the group consisting of sugar sources, pheromone, 4-methyl-3-hepatanone, pest-attractive organoborane derivatives, and other pest pheromones and their analogs, dry ice, bottled carbon dioxide, candle flames and other combustion flames, continuous and blinking white lights, black lights, green lights, and other colored lights.

7. The method according to claim 1 wherein said composition comprises about 20% by weight or less of said enzyme component.

8. The method according to claim 7 wherein said composition comprises about 0.1% to about 10% by weight of said enzyme component.

9. The method according to claim 8 wherein said composition comprises about 1% to about 5% by weight of said enzyme component.

10. The method according to claim 8 wherein said composition comprises about 5% by weight of said enzyme component.

11. The method according to claim 1 wherein said enzyme component further comprises an enzyme selected from the group consisting of oxidoreductases, transferases, hydrolases in addition to said protease, lyases, isomerases, ligases and mixtures thereof.

12. The method according to claim 11 wherein said enzyme is selected from the group consisting of hydrolases in addition to said protease, and mixtures thereof.

13. The method according to claim 12 wherein said enzyme is selected from the group consisting of lipases, glycosidases, cellulases, amylases, chitanses, and mixtures thereof.

14. The method according to claim 1 wherein said surfactant comprises a cationic, anionic, nonionic, zwitterionic, amphoteric, amphiphilic, or ampholytic surfactant, soaps, or mixtures thereof.

15. The method according to claim 14 wherein said surfactant comprises an alkali metal-, alkaline earth metal-, ammonium-, or alkylammonium-carboxylate, -sarcosinate, -sulfonate, or -sulfate salts of saturated or unsaturated alkyl, aryl, or alkylaryl compounds, the alkoxylated or polyalkoxylated compounds, the soaps, or the mixtures thereof.

16. The method according to claim 15 wherein said surfactant comprises a salt of saturated or unsaturated -alkyl alcohols, -fats, -fatty acids, or -oils, the ethyoxylated- or polyethoxylated-alkylphenols, -alcohols, -polyols, -fatty acids, -fatty acid amides, or -carboxylic acids, the soaps, or the mixtures thereof.

17. The method according to claim 16 wherein said surfactant comprises a salt of $C_8$–$C_{20}$ alcohol sulfates; salts of $C_8$–$C_{20}$ fatty acids; alkylaryl polyethylene glycols; natural soaps or neat soaps; insecticidal soaps or antibacterial soaps; oil soaps or castile soaps; household or commercial cleaners or degreasers; oil-, extract-, or saponified oil-spiked soaps.

18. The method according to claim 1 wherein said detergent builder comprises at least one of the alkali metal-borates, -tripolyphosphates, -pyrophosphates, -phosphates, -sesquicarbonates, -carbonates, -silicates, -aluminosilicates, nitrilotriacetates, -citrates, -EDTAtes, or mixtures thereof.

19. The method according to claim 1 wherein said composition comprises about 85% by dry weight or less of said detergent component.

20. The method according to claim 19 wherein said composition comprises about 75% by dry weight or less of said detergent component.

21. The method according to claim 19 wherein said detergent component comprises at least 50±25% by weight of said anionic surfactant(s) and as much as 50±25% by weight of said nonionic surfactant(s).

22. The method according to claim 19 wherein said detergent component provides about 25% or less by dry weight of at least one soap to the composition.

23. The method according to claim 22 wherein said detergent component provides about 5% to about 15% by dry weight of at least one soap to the composition.

24. The method according to claim 23 wherein said detergent component provides about 5% to about 10% by dry weight of at least one soap to the composition.

25. The method according to claim 1 wherein about 50% or less of said composition comprises detergent builder.

26. The method according to claim 25 wherein about 2% to about 10% of said composition comprises detergent builder.

27. The method according to claim 26 wherein about 5% of said composition comprises detergent builder.

28. The method according to claim 1 wherein said composition is in the form of an aqueous solution or suspension.

29. The method according to claim 28 wherein said composition comprises at least one enzyme-containing fermentation product.

30. The method according to claim 29 wherein said enzyme-containing fermentation product comprises the product of yeast fermentation of a mixture comprising a simple sugar source, a starch source, and a magnesium salt.

31. The method according to claim 30 wherein said sugar source comprises at least one of molasses, raw sugar. or mixtures thereof.

32. The method according to claim 30 wherein said yeast fermentation is carried out by at least one organism selected from the group consisting of *Saccharomyces cerevisiae* strains, *Saccharomyces carlsbergensis* strains, and mixtures thereof.

33. The method according to claim 30 wherein said magnesium salt is magnesium sulfate.

34. The method according to claim 29 wherein said composition comprises about 10% to about 65% by dry weight of said enzyme-containing fermentation product.

35. The method according to claim 34 wherein said composition comprises about 20% to about 50% by dry weight of said enzyme-containing fermentation product.

36. The method according to claim 35 wherein said composition comprises about 25% to about 50% by dry weight of said enzyme-containing fermentation product.

37. The method according to claim 30 wherein said composition comprises about 60% to about 99.5% by weight of water.

38. The method according to claim 1 wherein said composition has a pH of about 1 to about 12.

39. The method according to claim 38 wherein said composition has a pH of about 4 to about 10.

40. The method according to claim 38 wherein said composition has a pH which is set at the approximate optimal point for enzyme activity of the composition.

41. The method according to claim 38 wherein said composition has a pH which is set at the approximate optimal point for protease activity of the composition.

42. The method according to claim 38 wherein said composition further comprises at least one acid source or buffer.

43. The method according to claim 42 wherein said acid source is selected from the group consisting of acetic acid, citric acid, lactic acid, succinic acid, fumaric acid, tartaric acid, and phosphoric acid, and salts thereof, and mixtures thereof.

44. The method according to claim 42 wherein said composition comprises up to about 15% by weight of said acid source.

45. The method according to claim 43 wherein said acid source comprises citric acid and makes up about 0.5% to about 5% by dry weight of said composition.

46. The method according to claim 45 wherein said acid source comprises citric acid and makes up about 1% to about 2% by dry weight of said composition.

47. The method according to claim 43 wherein said acid source comprises lactic acid and makes up about 2% to about 10% by dry weight of said composition.

48. The method according to claim 47 wherein said acid source comprises lactic acid and makes up about 4% to about 8% by dry weight of said composition.

49. The method according to claim 1 wherein said composition further comprises at least one nitrogen source.

50. The method according to claim 49 wherein said nitrogen source is selected from the group consisting of urea, ammonium sulfate, and mixtures thereof.

51. The method according to claim 49 wherein Laid composition comprises up to about 45% by dry weight of said nitrogen source.

52. The method according to claim 50 wherein said composition comprises about 40% or less by dry weight of urea.

53. The method according to claim 52 wherein said composition comprises about 1% to about 30% by dry weight of urea.

54. The method according to claim 53 wherein said composition comprises about 5% to about 30% by dry weight of urea.

55. The method according to claim 54 wherein said composition comprises about 10% to about 30% by dry weight of urea.

56. The method according to claim 50 wherein said composition comprises about 30% or less by dry weight of ammonium sulfate.

57. The method according to claim 56 wherein said composition comprises about 0.5% to about 30% by dry weight of ammonium sulfate.

58. The method according to claim 57 wherein said composition comprises about 0.5% to about 20% by dry weight of ammonium sulfate.

59. The method according to claim 1 wherein said composition further comprises at least one of oils, extracts, or mixtures thereof.

60. The method according to claim 59 wherein said oil, extract, or mixture thereof comprises an oil or extract of citronella, pine cedarwood, sandalwood, wormwood, lemon grass, lemon or other citrus, lavendar, eucalyptus, sassafras, neem tree, balsam, niaouli, cajeput, clove, cubeb, thyme, garlic, wintergreen, peppermint or other mint, American wormseed, Levant wormseed, Juniperus spp., or Chrysanthemum spp.

61. The method according to claim 59 wherein said composition comprises up to about 5% by weight of at least one of said oils, extracts, or mixtures thereof.

62. The method according to claim 61 wherein said composition comprises about 0.1% to about 5% by dry weight of at least one of said oils, extracts, or mixtures thereof.

63. The method according to claim 1 wherein said composition further comprises an alcohol, hydrogen peroxide, glycerin, borax, pest hormones, growth regulators, or their analogs, botanical pesticides, soluble or suspendable aluminum compounds, or mixtures thereof.

64. The method according to claim 63 wherein said pest hormone, growth regulator, or analog is selected from the group consisting of methyl 12, 14-dihomojuvenate, methyl 12-homojuvenate, methoprene, hydroprene, fenoxycarb, lufenuron, diflubenzuron, hexaflumuron, cyromazine, growth regulators, and analogs, and mixtures thereof.

65. The method according to claim 63 wherein said botanical pesticide is selected from the group consisting of rotenone, ryanodine and other ryania extracts, sabadilla, hellebore, limonene, linalool, nicotene, and mixtures thereof.

66. The method according to claim 63 wherein said soluble or suspendable aluminum compound is selected from the group consisting of aluminum-halogen compounds, aluminum-silicon compounds, aluminum hydroxides, aluminum-containing organic compounds, aluminum-carbonate compounds, aluminum-phosphorus compounds, aluminum-sulfates and alums, aluminates, aluminum-nitrate compounds, and mixtures thereof.

67. The method according to claim 66 wherein said aluminum-containing organic compound is selected from the group consisting of aluminum carboxylates of the formula $Al(OH)_{3-n}(R)_n$ wherein n is 1, 2, or 3, and mixtures thereof.

68. The method according to claim 63 wherein said soluble or suspendable aluminum compound is selected from the group consisting of $AlCl_3$, $AlCl_3(H_2O)_6$, $Al_2(OH)_5Cl$, $AlCl_3O_9$, $Al[CO(NH_2)_2]_6SO_4I_3$, $Al_2(SiF_6)_3$, $MgAl_2(SiO_4)_2$, $Al(OH)_3$, aluminum diformate, aluminum diacetate, aluminum subacetate, $Al_2[C_{20}H_5(OH)(SO_3)_2]_3$, $Al_2(CO_3)_3$, $AlPO_4$, $Al_2(SO_4)_3$, $NaAl(SO_4)_2$, $NaAlO_2$, $Al(NO_3)_3$, $Al(OH)_2(NO_3)$, $Al(OH)(NO_3)_2$, and mixtures thereof.

69. The method according to claim 66 wherein said composition comprises a concentration of said soluble or suspendable aluminum compound sufficient to provide about 1% w/v or less of aluminum and at least about 50% of said aluminum is present as dissolved $Al^{3+}$.

70. The method according to claim 69 wherein said composition comprises a concentration of said soluble or suspendable aluminum compound sufficient to provide about 0.5% w/v or less of aluminum and at least about 50% of said aluminum is present as dissolved $Al^{3+}$.

71. The method according to claim 70 wherein said composition comprises a concentration of said soluble or suspendable aluminum compound sufficient to provide about 0.4% w/v of aluminum and substantially all of said aluminum is present as dissolved $Al^{3+}$.

72. The method according to claim 30 wherein said starch source is one of barley malt, oat malt, or a mixture thereof.

73. A method for exterminating pests comprising the steps of providing a composition comprising an enzyme component, said enzyme component comprising at least one protease, a detergent component comprising a surfactant and a detergent builder, a fermentation product of a starch source; and applying said composition to at least one pest.

74. The method of claim 1, wherein said composition includes baking soda.

75. The method according to claim 17 wherein said oil-, extract- or saponified oil-spiked soaps comprises at least one of: an oil, saponified oil, or extract of citronella, pine, cedarwood, sandalwood, wormwood, lemon grass, lemon or other citrus, lavender, eucalyptus, sassafras, neem tree, balsam, niaouli, cajeput, clove, cubeb, thyme, garlic, wintergreen, peppermint or other mint, American wormseed, Levant wormseed, Juniperus spp., or Chrysanthemum spp.

76. The method according to claim 17 wherein said oil-, extract-, or saponified oil-spiked soaps comprises at least one of: menthol, menthane, sobrerol, camphor, anethole, citronellol, rhodinol, or terpineol, or comprising a mixture thereof; or the mixtures thereof.

77. The method according to claim 60 wherein said oil, extract, or mixture thereof comprises at least one of: menthol, menthane, sobrerol, camphor, anethole, citronellol, rhodinol, or terpineol, or a mixture thereof.

\* \* \* \* \*